United States Patent
Voigt et al.

(10) Patent No.: US 7,560,720 B2
(45) Date of Patent: Jul. 14, 2009

(54) METHODS AND APPARATUSES OF DETECTING FOREIGN PARTICLES OR FAULTS IN A PLURALITY OF FILLED CONTAINERS

(75) Inventors: Aksel Voigt, Dianalund (DK); Per T. Sorensen, Sandved (DK); Henrik M. Nielsen, Naestved (DK)

(73) Assignee: Moller & Devicon A/S, Sandved (DK)

( * ) Notice: Subject to any disclaimer, the term of this patent is extended or adjusted under 35 U.S.C. 154(b) by 150 days.

(21) Appl. No.: 11/574,360

(22) PCT Filed: Aug. 29, 2005

(86) PCT No.: PCT/DK2005/000548

§ 371 (c)(1), (2), (4) Date: Sep. 4, 2007

(87) PCT Pub. No.: WO2006/021219

PCT Pub. Date: Mar. 2, 2006

(65) Prior Publication Data

US 2008/0001104 A1 Jan. 3, 2008

(30) Foreign Application Priority Data

Aug. 27, 2004 (EP) .................................. 04388058

(51) Int. Cl.
- *G01N 21/90* (2006.01)
- *G01N 21/88* (2006.01)
- *G06T 7/00* (2006.01)
- *H04N 7/18* (2006.01)

(52) U.S. Cl. .............................. 250/559.46; 250/223 B; 356/427; 356/240.1; 209/524; 348/127; 382/142

(58) Field of Classification Search ............ 250/559.46, 250/223 B; 356/240.1, 427, 428; 209/524, 209/526; 348/91, 127; 382/142

See application file for complete search history.

(56) References Cited

U.S. PATENT DOCUMENTS 3,598,907 A 8/1971 Drinkuth et al.

(Continued)

FOREIGN PATENT DOCUMENTS

| EP | 0 293 510 | 1/1993 |
| EP | 1 241 467 | 9/2002 |
| WO | WO 92/14142 | 8/1992 |

OTHER PUBLICATIONS

Hirzinger G. et al.; "A Fast Technique for Segmentation and Recognition of Binary Patterns"; Computer Society Conference on a Pattern Recognition and Image Processing; Dallas, Aug. 3-5, 1981; New York, IEEE, US, vol. Proc. 1981; Aug. 3, 1981, pp. 360-364, XP000605276.

*Primary Examiner*—John R Lee
(74) *Attorney, Agent, or Firm*—Klein, O'Neill & Singh, LLP

(57) ABSTRACT

A method of detecting unwanted objects or faults in containers containing a fluid or liquid includes: (a) moving the containers along a path of travel; (b) providing; a light source emitting light of a specific spectral distribution, wherein the containers and their contents are at least partly transparent or translucent at the specific spectral distribution; (c) providing a camera for detecting light at the specific spectral distribution, wherein (1) the path of travel intersects a field of view defined by the camera, and (2) the camera registers a sequence of digital images as the containers pass between the light source and the camera; (d) selecting a part of each of the digital images that corresponds to the outline of a specific container; and (e) processing a sequence of the parts of the digital images so as to detect the unwanted objects or faults in the specific container.

22 Claims, 7 Drawing Sheets

U.S. PATENT DOCUMENTS

| | | |
|---|---|---|
| 3,627,423 A | 12/1971 | Knapp et al. |
| 3,777,169 A | 12/1973 | Wlater et al |
| 4,095,904 A | 6/1978 | Klein et al. |
| 4,136,930 A | 1/1979 | Gomm et al. |
| 4,274,745 A | 6/1981 | Takahashi et al. |
| 4,679,075 A | 7/1987 | Williams et al. |
| 4,750,035 A | 6/1988 | Chang et al. |
| 4,915,237 A | 4/1990 | Chang et al. |
| 4,959,537 A | 9/1990 | Kimoto et al. |
| 5,067,616 A | 11/1991 | Plester et al. |
| 5,095,204 A * | 3/1992 | Novini .................. 250/223 B |
| 5,365,343 A | 11/1994 | Knapp |
| 5,523,560 A | 6/1996 | Manique et al. |
| 5,694,221 A | 12/1997 | Knapp |
| 6,226,081 B1 | 5/2001 | Fantone et al. |
| 6,275,603 B1 | 8/2001 | Cronshaw et al. |
| 6,498,645 B1 | 12/2002 | Knapp et al. |
| 2008/0001104 A1* | 1/2008 | Voigt et al. ............. 250/559.46 |

* cited by examiner

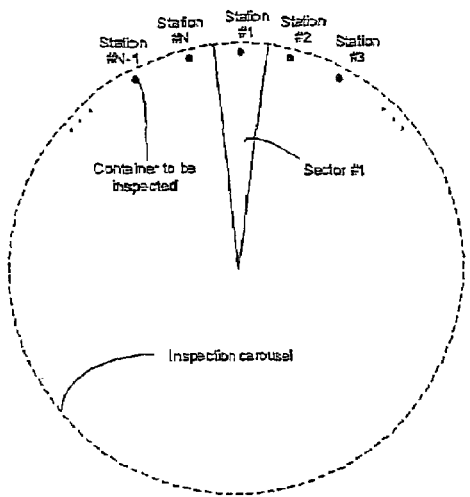
Fig. 8
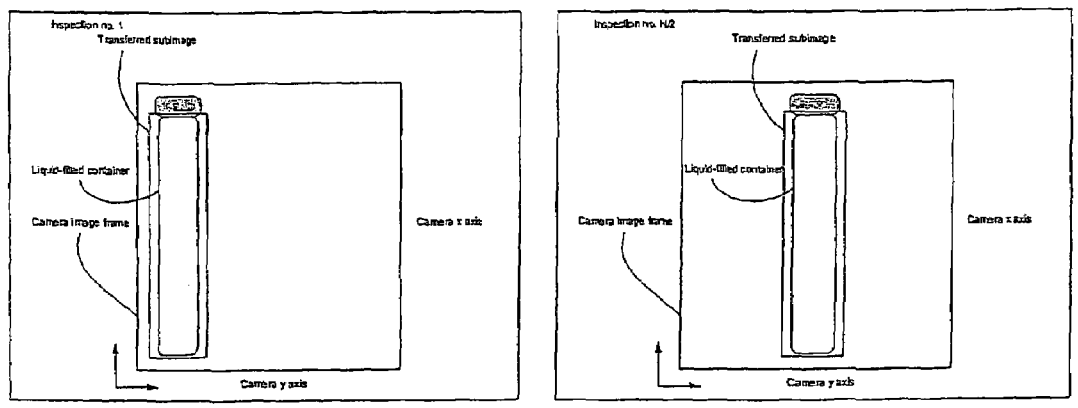
Fig. 9a
Fig. 9b
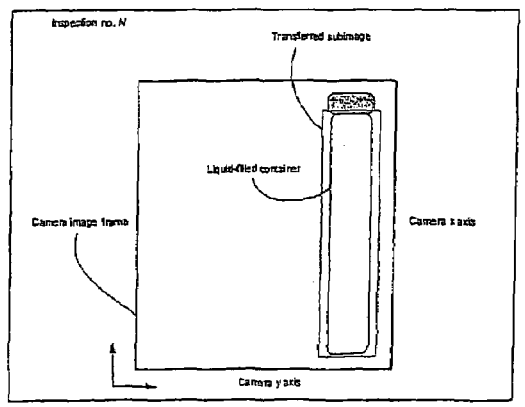
Fig. 9c

METHODS AND APPARATUSES OF DETECTING FOREIGN PARTICLES OR FAULTS IN A PLURALITY OF FILLED CONTAINERS

CROSS-REFERENCE TO RELATED APPLICATION

This application is a national phase filing, under 35 U.S.C. §371(c), of International Application No. PCT/DK2005/000548, filed Aug. 29, 2005, the disclosure of which is incorporated herein by reference in its entirety.

FEDERALLY SPONSORED RESEARCH OR DEVELOPMENT

Not Applicable

FIELD OF THE INVENTION

The present invention relates to methods of detecting unwanted objects or faults in a plurality of containers including a substance. In the present context, the term substance is to be considered covering fluids, liquids, powders, granular materials, freeze dried substances, emulsions, suspensions or any combinations thereof, also the terms will be used individually while covering all of the mentioned terms. The object or objects may be found on or in the containers. The fault or faults may be found in the material used to produce the containers or on the containers.

BACKGROUND OF THE INVENTION

Methods for detecting unwanted objects or faults in containers have been described in related patent publications such as WO 92/14142, EP 0 293 510, U.S. Pat. Nos. 4,095,904, 4,136,930, 3,598,907, 3,777,169, 4,274,745, 5,365,343, 3,627,423, EP 1 241 467, U.S. Pat. Nos. 5,523,560, 5,694,221, 6,226,081, 4,750,035, 4,959,537, 5,067,616, 4,915,237 and 6,498,645. The disclosures of the aforementioned US patents are hereby incorporated in the present specification by reference.

Some apparatuses and methods for detecting unwanted objects, i.e. contamination, and faults in containers including a fluid or liquid described earlier relied on line scanners. Also cameras have been used. Most of the machines have been configured so that the camera or line scanner and/or the light source were movable for enabling more than one scan or detection per container, possibly causing vibration and requiring complicated machinery.

SUMMARY OF THE INVENTION

The present invention provides, according to a first aspect of the present invention, a method for detecting unwanted objects or faults in a plurality of containers comprising the steps of:

providing a path of travel along which the plurality of containers being conveyed, moving the plurality of containers along the path of travel, providing a light source emitting light of a specific spectral distribution, the light source being positioned at one side of the path of travel, the containers being at least partly transparent or translucent to light at the specific spectral distribution, the fluid or liquid being at least partly transparent or translucent to light at the specific spectral distribution, providing a first camera including a CMOS chip for detecting light at the specific spectral distribution emitted from the light source, the first camera defining a field of view, the path of travel intersecting the field of view, the CMOS chip producing a digital image comprising a specific number of pixels, rotating each of the containers in either clock-wise or counter-clock-wise direction so as to bring the fluid contained in each of the containers in motion, stopping the rotation of each of the containers prior to each of the containers entering the field of view, the fluid still rotating, alternatively, stopping the rotation of each of the containers after each of the containers entering the field of view, the fluid still rotating, the first camera registering a sequence of digital images as the container passes between the light source and the camera, selecting a part of each of the digital images, the part substantially corresponding to the outline of a specific container, transmitting each of the parts to a digital image processing unit, the digital image processing unit processing the sequence of parts of digital images so as to detect the unwanted objects or faults in the specific container, the processing resulting in either an establishment of an object or fault present or not present in the specific container.

The camera including a CMOS chip detects the light admitted by the light source. As the light from the light source is of a special or specific spectral distribution, the camera, or the CMOS chip in the camera, needs to be sensitive to light or radiation admitted in that spectral distribution, i.e. within that frequency spectrum or interval. The CMOS chip may be sensitive to light outside the spectral distribution of the light admitted by the light source as well as the light source admitting light at frequencies outside the frequency spectrum that the CMOS chip is sensitive to. The images obtained by the camera are inspected and/or analysed, specifically, the images analysed to detect faults or objects on or in the container.

In the present context the term container is to be construed as a generic term covering all containers, bottles, receptacles, receivers, vessels capable of receiving and storing a substance, such as a fluid or a liquid. The containers may be opened, closed or sealed in some manner. The container may e.g. be ampoules, cartridges, vials, syringes or other containers.

The light source provided may be any source of electromagnetic radiation, providing electromagnetic radiation of a specific spectral distribution. The distribution may be within the visible spectrum, but may also include infrared, near infrared, ultra violet and electromagnetic radiation of other wavelengths.

Rotation of the containers at a sufficiently high speed is contemplated to whirl any particles or objects that may be fastened to the inside of the container, e.g. at the bottom or side wall of the container, into the fluid or liquid.

The rotation of the containers may be performed according to a specific rotation profile including rotations in both clock-wise and counter-clock-wise directions as well as varying speeds other than those speeds achieved during acceleration of the rotation. In one embodiment, the rotation profile may include one period of rotating in clock-wise direction followed by one period of rotation in counter-clock-wise direction.

The speed of rotation may be varied from 0 to 10,000 rpm or anywhere in-between or above. Higher rotation speeds may be used for specific applications. The choice of rotation speed may depend on the substance comprised in the container; high viscosity fluids or liquids may be spun faster than low viscosity fluids or liquids. Also, the amount of fluid or liquid in the container may influence the choice of rotation speed.

The containers are rotated according to a rotation profile in order to: A) Re-suspend the liquid in case of suspension liquids. B) Shake loose possible particles in the liquid. C) Make the liquid and possible particles rotate within the container to facilitate detection. D) Shake loose possible air bubbles in the container so that they are not detected as particles. Air bubbles may be allowed to be in the liquid, but from a particle detection point of view they are highly undesired as they are easy to misinterpret as particles thus increasing the false rejection rate.

Air bubbles may be present in a fluid or liquid after filling the container. These air bubbles may be loosened or removed from e.g. an inner wall of the container prior to the inspection by rotating the container. The presence of air bubbles could be interpreted by an inspection machine performing visual inspections as faults, defects or foreign matter. The frequency of presence of air bubbles is contemplated to be increased provided the inspection machine is placed e.g. in-line with a filling machine.

The decision when or if to stop the containers rotating, may be based on an assumption on the likelihood of faults or defects in the container to be hidden from the camera when not rotating the container.

In an alternative embodiment of the present invention, the light source and the camera may be positioned at the same side of the path of travel. The light source in any of the embodiments of the present invention may be positioned elevated or lowered compared to the camera device or devices. Preferably, the light source directly illuminates at least one container. Alternatively the light may be directed from the light source to the container using prisms and/or filters and/or mirrors and/or wave guides.

The light may be positioned in an elevated position relative to the container so that the light source e.g. illuminates the container at an angle different from 90° to a rotation axis or longitudinal axis of the container. Also, the light emitted by the light source may pass through filters, such as polarization filters linear, circular or other polarization, color filters or other filters, before/or after illuminating the container. Different positions of the light source relative to the container is contemplated to be advantageous in detecting different kinds of objects or faults, such as fibers or defects in the material making up the container.

Different positions of the light source relative to the container is contemplated to be advantageous in detecting different kinds of objects or faults, such as fibres or defects in the material making up the container.

The camera may include any kind of light sensitive device for recording a digital image; in the presently preferred embodiment of the present invention a CMOS chip is employed, specifically a CMOS matrix image sensor. As stated, the device must be sensitive to at least part of the radiation spectrum of the electromagnetic radiation emitted by the light source. The camera may be constituted by any device capable of converting light at the specific spectral distribution into digital images in two dimensions.

Particularly, the electromagnetic radiation may be polarised, such as linearly polarised, circularly polarised, horizontally or vertically polarised or any combinations thereof. Also, filters may be positioned at or on the camera or light source.

The camera device may record a sequence of images as a specific container is conveyed along the path. The sequence of images, or part of the images, may then be transmitted to an image processing unit, such as a personal computer, a specialised computer or a workstation. Also, an image processing unit may be built into the camera, so that the information delivered by the camera may be an indication of whether an object or fault has been detected in a specific container.

The rotation of a container also allows for inspection of e.g. a freeze dried substance where light is not able to pass through, meaning that a visual inspection of the surface defined by the frozen or freeze-dried substance inside the container is possible by rotating the container.

It is contemplated that it may be possible to detect and distinguish break lines in the frozen or freeze-dried substance from faults and/or objects.

Medication or medicine is sometimes produced, delivered, and/or stored as a solid, e.g. in the form of a powder, freeze-dried state or as a granular material.

An emulsion may include one or more balls of oil, and these balls of oil may be detected and not classified as unwanted objects or faults.

The images transmitted may be the entire image recorded by the camera, however, this transmission of digital information may exceed the limitations of the equipment used to transmit and receive the images, e.g. via a PCI-bus, a cPCI-bus, a PCI-X bus, PCI-express or the like. Therefore, in the presently preferred embodiment of the present invention, only a sub-image, or part of an image, is transmitted instead of the entire image. This limits the amount of data transmitted from the camera, or a device attached to the camera, to the image-processing unit. In the presently preferred embodiment of the present invention, the part of the image that is selected is rectangular or square. Other sub-images than rectangular or square may be envisioned, such as sub-images precisely corresponding to the outline of a container. Also, dynamic outlines may be utilised, automatically detecting the outline of a specific container.

Embodiments where the images transferred or transmitted are differential images, i.e. the transmitted image is a subtraction of the actual image recorded and e.g. the previous image, are also considered part of the present invention. The image transmission is preferably a loss-less transmission.

Preferably the entire light sensitive device, i.e. the CMOS chip, is illuminated and quantified/digitised for creating an image having as high a resolution as possible. The higher the resolution is, the more detailed the inspection could be.

The camera may record images in color, such as RGB, but compared to recording images in greyscale or black and white, the color images include more data for representing the colors. Preferably black and white or greyscale images are recorded.

The image processing unit, as mentioned above, preferably being a computer, such as a personal computer, workstation, specialised computer or a unit built into the camera device, receives the data representing the digital images either directly from the camera or via a device attached to or built into the camera that controls the selection of the sub-image.

The sub-image must be controlled since the container is moved across the field of view of the camera. Preferably the container is moved substantially along a horizontal axis in front of the camera. The container will most likely only fill part of the image and therefore the sub-image must be selected in order to obtain a number of useful sub-images to be processed. The position of the sub-image may be controlled in a number of ways. The sub-image may be controlled by an external controller registering the position of the container to be inspected. Thereafter the external controller may send instructions to the camera recording the images that the sub-image is to be moved or shifted.

According to a first advantage of the present invention, the processing may be constituted by the digital image-processing unit comparing at least two of the parts of two specific digital images to detect unwanted objects or faults in the specific container. Comparing two sub-images or image parts enables the image-processing unit to determine if any inconsistencies are found between the two images. These possible inconsistencies may then be interpreted as faults in the container or the presses of unwanted objects, viz. foreign matter, dirt, particles or other items.

According to the teachings of the present invention, a second advantage relates to the digital image-processing unit analysing at least one digital image to detect unwanted objects or faults in the specific container. The image analysing unit may analyse at least a single image in the sequence of images, or a sub-image thereof, by analysing one or a group of pixels in the digital image or part of a digital image to determine if a fault or object is present. Pixels is the term used to describe the individual components constituting the digital image. Techniques relating to digital image analysis of this sort are described in other publications.

A third advantage of the present invention relates to the processing being constituted by a subtraction of two images or sub-images in sequence or out of sequence. Subtracting two images results in an image showing the difference between the two images. The differences may then be interpreted as either unwanted objects or faults, alternatively as merely errors in the recording of the images.

A fourth advantage of the present invention relates to the processing being constituted by a comparison of the part of a specific digital image to a reference image for detecting unwanted objects or faults in the specific container. A reference image may be constituted by an image or part of an image being calculated as an average of a set or sequence of images or parts of images. Alternatively, the reference image may be pre-recorded and stored. The reference image is then required to be of a container without errors or faults, and without unwanted objects or foreign matter.

According to a second feature of the present invention, the containers may be conveyed at a substantial constant speed along the path of travel. This means that the conveyor conveying the containers maintains substantially the same speed during operation of the inspection machine. When starting up or shutting down the machine, the conveyor accelerates to obtain the desired speed. Alternatively, the conveyor may be intermittent.

According to the teachings of the present invention, the method according to the first aspect may further comprise the steps of:

providing a second camera including a second CMOS chip for detecting light at the specific spectral distribution emitted from a second light source, a second line of sight being defined between the second light source and the second camera, the path of travel intersecting the second line of sight, the second CMOS chip producing a digital image comprising a second specific number of pixels, the second camera registering a second sequence of frames constituting a second multitude of digital images as the container passes between the second light source and the second camera, selecting a second part of each of the digital images of the second sequence, the second part substantially corresponding to the outline of the specific container, transmitting each of the second parts to the digital image processing unit, the digital image processing unit processing the parts of the second multitude of digital images so as to detect the unwanted objects or faults in the specific container, comparing the result of the second processing to the first processing in order to confirm the result of the first processing.

The method may also incorporate any of the other features or advantages mentioned in this description.

Providing a second camera to the inspection machine enables a procedure where a double check of the inspection is possible. Surprisingly, a second camera increases the percentage of correct identifications of containers having faults or including foreign matter, dirt or the like. The images from the second camera may be processed similarly to the images from the first camera.

The two cameras may be adapted for performing the same type of inspection of the containers, i.e. detecting the same kinds of faults or defects, such as faults or defects in the material or object present in the container or in the material constituting the container or on the surface of the container. In addition, two additional cameras may be provided so that the full set-up includes four cameras where the cameras in pairs perform inspections for detecting similar faults or errors, e.g. two cameras may inspect the containers for foreign objects while the other two cameras perform inspections for detecting faults in the container.

As described elsewhere, the position of the light source may have influence on which type of inspection may be performed and in the set-up described above with four cameras, two light sources may be provided for one kind of inspection while two other light sources may be provided for performing other types of inspection.

Alternatively, three cameras may be set up for performing identical or the same types of inspections while the fourth performs a different kind of inspection. Further alternatively, all four cameras may be used for performing the same type of inspections. Using two cameras for performing the same type of inspection having two cameras enables the possibility of validating or checking the result of the first inspection.

As also described elsewhere, the containers may be spun in accordance with a specific spinning profile where the provision of two cameras may be used in a profile including spinning, stopping, inspecting followed by spinning, stopping and inspecting each of the containers. The spinning steps or states may include spinnings in one or both directions, i.e. clockwise and counter-clock-wise or combinations thereof and may include spinnings at varying speeds.

In one embodiment of the present invention, the container is spun one revolution, i.e. 360° where a series of images, such as 4-14, such as 6-12, preferably 8-10 images, are recorded for inspection of the outside of the container. Preferably more than three images are recorded and analysed for ensuring that the entire surface of the container is covered by the images. In alternative embodiments other numbers of images may be recorded. The entire image may be used, as well as only a part of each image.

In the presently preferred embodiment of the present invention, the two cameras or the signal acquisition and signal processing units, may be substantially identical. However, embodiments where the two cameras or the signal acquisition and signal processing units are not identical are considered part of the present invention. The cameras may, for example, be sensitive to different wavelengths, possibly allowing inspections to detect items, objects, dirt or the like, not visible to one camera at one wavelength to be detected by a second camera at a different wavelength.

Further, embodiments including more than two cameras may be envisioned.

A first object of the present invention relates to the processing of the first multitude of digital images resulting in an establishment of an object or fault present and provided processing of the second multitude of digital images resulting in an establishment of an object or fault present the specific container being rejected.

If the image-processing of the images from the two or more cameras result in detection of foreign matter or faults, the container may be rejected, discarded or abandoned.

A second object of the present invention relates to the processing of the first multitude of digital images resulting in an establishment of no object or fault present and provided processing of the second multitude of digital images result in an establishment of an object or fault present the specific container being reanalysed.

A third object of the present invention relates to the processing of the first multitude of digital images resulting in an establishment of an object or fault present and provided processing of the second multitude of digital images result in an establishment of no object or fault present the specific container being reanalysed.

If the image-processing of the images from the two or more cameras do not result in the same outcome or detection of faults or objects present in the container, the container may be recycled into the inspection apparatus, thereby reducing the number of false rejects, i.e. containers where the inspection has falsely identified a container as having a fault or an unwanted object. Also, the establishment of no faults or unwanted objects present in the container is made more securely, thereby reducing the number of false accepts. A fourth object of the present invention relates to the processing of the first multitude of digital images resulting in no establishment of an object or fault present and the processing of the second multitude of digital images resulting in an establishment of no object or fault present in the specific container being passed on for further processing.

The further processing may be packaging, further treatment or the like.

According to a second aspect of the present invention, a method of detecting unwanted objects or faults in a plurality of containers including a fluid or liquid is provided. The method according to the second aspect of the present invention may comprise the steps of:
  providing a path of travel along which the plurality of containers be conveyed,
  moving the plurality of containers along the path of travel,
  providing a first light source emitting light of a specific spectral distribution, the light source being positioned at one side of the path of travel, the containers being at least partly transparent or translucent to light at the specific spectral distribution, the fluid or liquid being at least partly transparent or translucent to light at the specific spectral distribution,
  providing a second light source emitting light of the specific spectral distribution, the second light source being positioned at one side of the path of travel,
  providing a first light detection device for detecting light at the specific spectral distribution emitted from the first light source, the first light detection device defining a first field of view, the path of travel intersecting the first field of view, the first light detection device producing a first digital image comprising a specific number of pixels,
  providing a second light detection device for detecting light at the specific spectral distribution emitted from the second light source, the second light detection device defining a second field of view, the path of travel intersecting the second field of view, the second light detection device producing a second digital image comprising a second specific number of pixels,
  the first and the second light detection device registering a first and second sequence of digital images as the container passes the first and the second field of view respectively,
  selecting a part of each of the digital images of the first and the second sequence, the part substantially corresponding to the outline of a specific container,
  transmitting each of the parts to a digital image processing unit,
  the digital image processing unit processing each of the digital images so as to detect the unwanted objects or faults in the specific container,
  the processing resulting in either an establishment of an object or fault present or not present in the specific container.

In one embodiment of the present invention, the first light detection device being positioned opposite the first light source so that the first light source is in the first field of view and/or the second light detection device being positioned opposite the second light source so that the second light source is in the second field of view.

The light detection devices may be constituted by any device capable of converting radiation of the specific spectral distribution into a signal, such as a digital signal or analogue signal.

It is a particular advantage of the present invention, that the first and the second light detection units of the method according to the second aspect of the present invention may be constituted by cameras each including at least one CMOS chip of producing the first and the second digital images. Alternatively, the first and second cameras may include any unit or chip capable of converting radiation of the specific spectral distribution into digital images in two dimensions.

The method according to the second aspect of the present invention may comprise any of the objects, features and/or advantages mentioned in relation to the first aspect of the present invention.

According to a third aspect of the present invention, an apparatus for detecting unwanted objects or faults in a plurality of containers including a fluid or liquid is provided, the apparatus comprising:
  a frame,
  a conveyor mounted in the frame constituting a path of travel for the plurality of containers, the conveyor defining an input and a corresponding output, the input receiving the plurality of containers, the output outputting the plurality of containers,
  a first light source emitting light of a specific spectral distribution mounted in the frame, the first light source being positioned at one side of the path of travel, the containers being at least partly transparent or translucent to light at the specific spectral distribution, the fluid or liquid being at least partly transparent or translucent to light at the specific spectral distribution,
  a first camera including a first CMOS chip for detecting light at the specific spectral distribution emitted from the first light source, the first camera defining a first field of view, the first camera be mounted to the frame opposite the first light source so that the first light source is in the first field of view, the path of travel intersecting the first field of view, the first CMOS chip producing a first digital image comprising a first specific number of pixels, the first camera registering a first sequence of digital images as a specific container passes the first field of view, a first digital image processing unit electrically connected to the first camera, the camera selecting a part of each of the digital images substantially corresponding to the outline of a specific container and transmitting the part to the digital image processing unit, the digital image processing unit processing the sequence of parts of digital images so as to detect the unwanted objects or faults in the specific container, the processing resulting in either an establishment of an object or fault present or not present in the specific container.

The reference to the camera making a selection is to be construed as an electronic device built into or attached to the camera that makes the selection of a part of the image recorded by the camera. This selected part of the image recorded by the camera is then transmitted to an image processing unit, such as a computer, workstation, specialised image analysis apparatus, an embedded computer or an image processing device in the camera.

Electrical connections is in the present context to be construed as a generic term covering all kinds of connections where transmission of data is possible, e.g. wired connections, wireless connections, fibre-optical connections, or combinations thereof.

According to a third feature of the present invention, the conveyor may be constituted by a conveyor chosen from the group comprising at least rotating carrousels, belt conveyors and chain conveyors. Other conveyors may be used, such as conveyors having suction cup holders. The material used to form the conveyor may be plastic or a metallic material, such as stainless steel or the like. A specific conveyor may be adapted of receiving a bottle or container defining size within an interval, thereby not limiting the capability of the carrousel to receive only one specific size of containers.

A fourth feature of the present invention relates to the conveyor being directly driven by a servo motor, step motor or a linear motor, alternatively, a gear means may be used. The motor is preferably of a sort delivering a constant torque so that the operation of the conveyor may be substantially constant.

According to a third object of the present invention, each of the containers may be rotated in either clock-wise or counter-clockwise direction by rotating means so as to bring the fluid contained in each of the containers in motion. The rotating means may be constituted by an electric motor or the like. The rotating means must preferably be able to rotate the container at a sufficiently high speed so that possible objects or foreign matter inside each of the containers may be loosened and detected in the fluid or liquid.

A fifth feature of the present invention relates to the inspection apparatus further comprising:

a second light source emitting light of the specific spectral distribution mounted in the frame, the second light source being positioned at one side of the path of travel; and a second camera including a second CMOS chip for detecting light at the specific spectral distribution emitted from the second light source, the second camera defining a second field of view, the path of travel intersecting the second field of view, the second CMOS chip producing a second digital image comprising a second specific number of pixels, the second camera registering a second sequence of digital images as the specific container passes the second field of view.

By providing a second light source and a second camera, the validation may be performed at a distance to the inspection performed by the first camera. In between the two inspections, the container may be spun again for ensuring that the liquid or fluid is in motion at the time when the second inspection is made. Alternatively, the inspection is made close enough to the first inspection for the fluid or liquid to be considered being in motion at approximately the same speed. In reality, the liquid or fluid may have slowed down so much that a second spinning of the container is required. This, however, depends on the viscosity of the fluid or liquid.

Generally, a second camera or detection device enables a validation of the inspection of the first camera. Since there is a possibility that the inspection is to be erroneous, a validation of the first inspection will eliminate some of the possibility of making errors.

A sixth feature of the present invention relates to the inspection apparatus further comprising:

a second camera including a second CMOS chip for detecting light at the specific spectral distribution emitted from the first light source, the second camera defining a second field of view, the second CMOS chip producing a second digital image comprising a second specific number of pixels, the second camera registering a second sequence of digital images as the specific container passes the second field of view.

The second camera may be provided and positioned close to the first camera and directed at the first light source so that the second camera performs its inspection on the same specific container as the first camera at substantially the same period of time. The light source may also define an area so that the two cameras may be directed differently, but still at the first light source, while inspection different containers at the same point in time.

A seventh feature of the present invention relates to the second camera being electrically connected to the first digital image processing unit. Alternatively, the apparatus may further comprise a second digital image processing unit, and the second camera may be electrically connected to the second digital image processing unit, and, a part of each of the second digital images substantially corresponding to the outline of a specific container transmitted to the digital image processing unit, the first or the second digital image processing unit processing the second sequence of digital images so as to detect the unwanted objects or faults in the specific container, the processing resulting in either an establishment of an object or fault present or not present in the specific container.

The choice of number of image processing units depends on the amount of data processing power, i.e. how many instructions pr. unit of time the image processing unit may perform, as compared to the actual amount of processing required in a given period of time before a decision is required. This depends partly on the number of pixels in the specific image or part of the image that is to be processed and on the algorithm chosen to perform the image analysis.

It is a specific object of the present invention to provide means for moving a specific container from the outlet to the inlet. Provided the inspection of two or more cameras has resulted in different outcomes, the container may be returned to be inspected by the cameras again. Thereby, the number of false rejects may be reduced and thereby the waste of money and material may be decreased.

According to an eight feature of the present invention, the path of travel may define an input and a corresponding output, the input receiving the plurality of containers, the output outputting the plurality of containers, a return conveyor for conveying specific containers from the output to the input. The return conveyor may be constituted by a rotating carrousel, belt conveyor, chain conveyor, wheel or any combinations thereof.

Containers may be inputted to the conveyor at any point and retracted or outputted at any point. One example of this is an embodiment where a conveyor conveys containers cyclically and inspections are carried out at one or more locations. After the inspection has determined either no objects or faults present or objects or faults present in a specific container the container may be removed from the conveyor. In an embodiment where two inspections are carried out, a container where the two inspections have resulted in different outcomes or decisions, the container may simply be left on the conveyor to be re-inspected. Two stations may remove and insert containers. The insertion may be restricted to positions where an available holder or place exists.

BRIEF DESCRIPTION OF THE DRAWINGS

The invention is now to be further detailed described, with reference to the attached drawings, in which:

FIG. 8 is a schematic illustration of an inspection carrousel, and FIGS. 9a-9c are schematic views of sub-image selections.

DETAILED DESCRIPTION OF THE INVENTION

Figure 1:
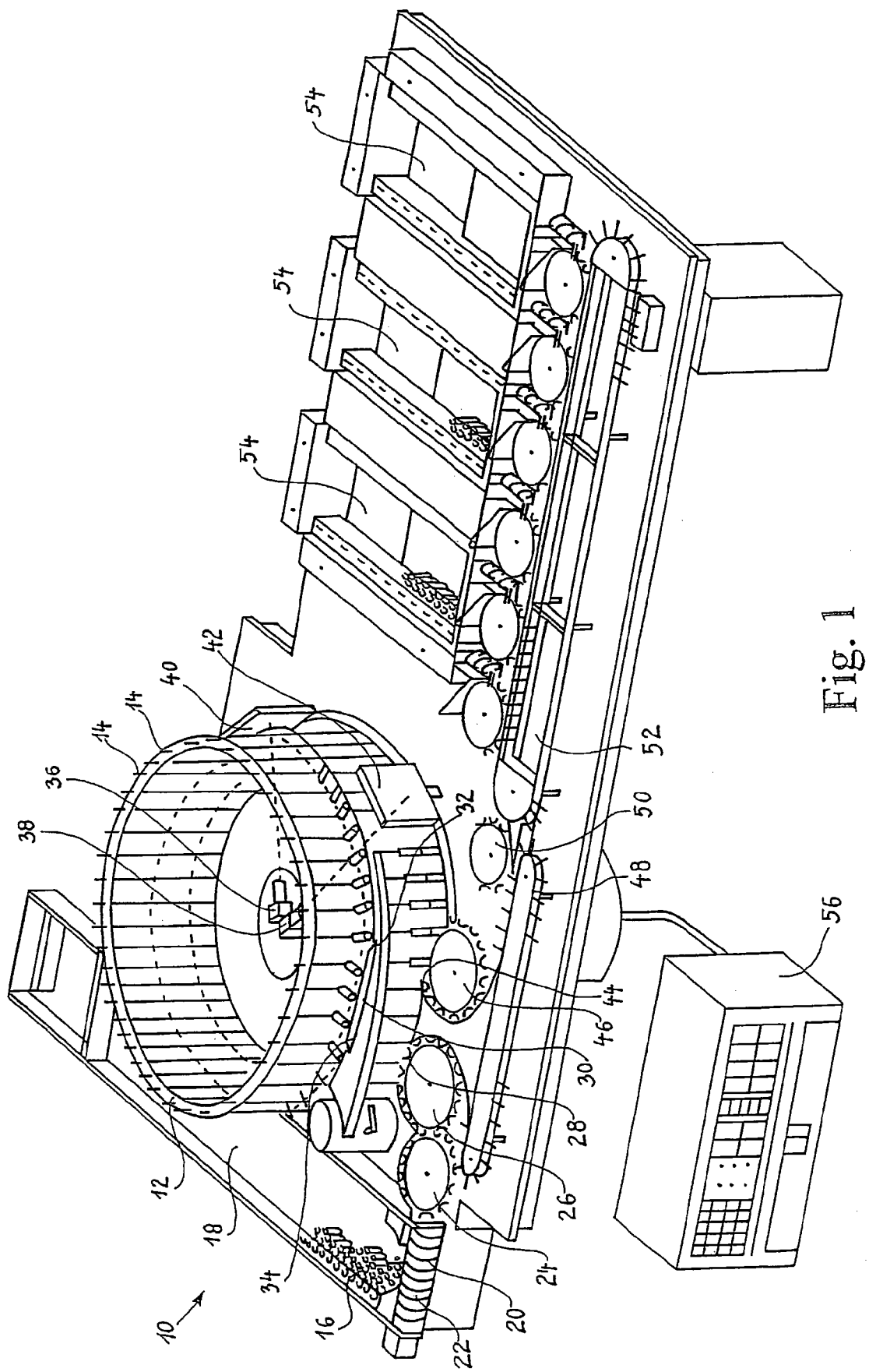
FIG. 1 is a schematic elevated view of an inspection machine according to the present invention.

In FIG. 1, an inspection machine 10 is schematically illustrated. The inspection machine 10 visually inspects containers 16 for detecting faults in the material used to form the individual container 16, and it inspects the containers 16 for determining if any unwanted objects or foreign matter is present inside the containers 16. Since the inspection machine 10 is based on visual inspections, the machine may also detect any objects or foreign matter that may be present on the outside of the containers 16.

The containers 16 are loaded from a storage or feeding system 18 through a screw 20 having a track 22, substantially corresponding to the diameter of an individual container 16.

The containers 16 are received from the track 22 into a first wheel 24. The first wheel 24 comprises holding mechanisms such as suction devices or grabbing devices.

The containers 16 are transferred from the first wheel 24 to a second wheel 26, preferably having the same overall structure as the first wheel 24. The second wheel is rotated in the opposite direction as compared to the first wheel 24. The second wheel 26 delivers the individual containers 16 at a drop point 28 where the individual containers 16 are received in a carrousel 12 comprising a plurality of holders all designated the reference numeral 14. All of the holders in the carrousel 12 are identical and are therefore given the same reference numeral.

The individual holders 14 comprise a motor for rotating the containers 16 received in the holder 14. The holder 14 may rotate the containers 16 in either a clockwise or counter-clockwise direction around an axis, preferably the longitudinal axis of the containers 16.

A specific rotation profile may be supplied for rotating the containers at specific rotation speeds including clockwise and/or counter-clockwise directions. The containers 16 are rotated so as to re-suspend the fluid and/or material found in the fluid in the container 16. In the centre of the carrousel 12 one or more cameras may be placed to perform the visual inspection of the individual containers 16. In the presently preferred embodiment of the present invention two cameras 36 and 38 are placed in the centre of the carrousel 12. The cameras 36, 38 define an angle between them. The angle between the cameras, i.e. between the fields of views defined by the cameras 36, 38, is in the presently preferred embodiment of the present invention 20-60°.

The angles between the cameras may be different from described above as the cameras in one embodiment may be placed along the centre of rotation of the carrousel 12 with the field of view pointing towards the bottom of the carrousel 12 whereon a reflector such as a mirror has been placed for the camera to inspect the container 16. The angle between the fields of views of the cameras may be from 0 to 180°. The placement of the cameras in such set-up may be necessary for the placement of two cameras with the carrousel at one time. Also, this configuration may enable more cameras such as four cameras to be placed within the carrousel 12 at one time. At the same time, the cameras are protected within the carrousel from outside influences such as persons bumping into the cameras and thereby possibly moving or shifting or rotating the cameras so that the cameras do not inspect the proper or correct container 16.

Embodiments with one camera may have the camera placed anywhere within the carrousel or outside the carrousel. Embodiments with two or more cameras may have the cameras in other positions than the centre of the carrousel, e.g. two cameras positioned on top of each other, inspecting either the same container or bottle at one time or two or more different containers at one time.

In other embodiments, cameras may be placed opposite to the centre of the carrousel, such as described above concerning the cameras being placed along the rotation axis of the carrousel 12 the cameras are placed off-set to the rotation axis of the carrousel and thereby not at the exact centre of the carrousel In an alternative embodiment of the present invention, the cameras 36, 38 may be placed on top of each other directed in substantially the same direction so that the two cameras inspect the same specific container 16 at the same time or two different parts of a specific container, e.g. provided the containers are too large to be inspected by a single camera.

An advantage of having two cameras is that the second camera may be used to verify the inspection made by the first camera. Provided that the first camera has determined that no objects or faults are present in a specific container, the second camera should come to the same decision, however, provided that the first camera missed an object or fault in the container 16, and provided the second camera identifies this object or fault, the container may be recycled and reanalysed to securely establish whether an object or fault is present in the container 16.

The analysis of the images from the first and the second camera must result in the same conclusion for both sets of images in order for the container 16 to be either discarded or sent on for further processing. If the image analysis process performed on the images from either the first or the second camera results in an establishment of an object or fault present, alternatively no object or fault present, different from the result obtained by the image processing performed on the images from the other camera, the container 16 is recycled to be analysed by the two cameras again. This recycling process is contemplated to reduce the number of false rejects, i.e. situations where a container is rejected even though the container should have been passed, also situations where a container is passed on, even though the container should have been rejected, is contemplated to be reduced, i.e. false accepts.

In the presently preferred embodiment of the present invention, an algorithm for processing the digital images or parts of digital images as described below is implemented.

Everything, which causes some contrast within a small area of interest (AOI), is declared to be part of a particle or anomaly, except if it remains on (nearly) the same position in all images of the sequence (static anomalies, e.g. dirt on the container surface). Some contrast means that the difference between the brightest and darkest pixel lies above a certain threshold.

Data Objects:

IM_PROTO: prototype image, used as reference for placing AOI's alignment of images within an image sequence AOI_LIN_LOC: area of interest for locator, which is responsible for alignment AOI_PI: area of interest defining the active area for particle inspection IM_SRC [N]: the recorded image sequence—set of grey value images (of a container)

IM_SRC_FIL [N]: improved source images IM_SRC [N] (reduction of errors introduced by the camera CMOS chip)

IM_SRC_MEAN [N]: low-pass filtered images of IM_SRC_FIL [N]

IM_DIFF [N]: set of difference images IM_SRC_MEAN [N]–IM_SRC_FIL [N] ("local contrast" images)

IM_BIN_RAW [N]: set of binary images resulting from thresholding the IM_DIFF [i] images (two thresholds defining an interval)

pixel value IM_BIN_RAW [i][y][x]==0: no anomaly
pixel value IM_BIN_RAW [i][y][x]!=0: anomaly IM_BIN [N]: set of binary images, same as IM_BIN_RAW [i], but aligned now IM_BIN_EXT [N]: set of binary images, same as IM_BIN [i], but with static anomalies removed IM_MASK [N]: set of binary images, "dilated" version of IM_BIN [i].

IM_ACCU: helper image for the generation of the image IM_MASK_STATICS

A pixel value of 0 indicates, that there was not detected any anomaly.

A pixel value of 1 indicates, that at this position there was once an anomaly detected (nearby)

A pixel value of N indicates, that at this position there were only anomalies detected IM_MASK_STATICS: image, which is used to "ignore" some locations within an image, where the system was able to detect static anomalies A pixel value of 0 indicates: at this place there is most certainly a static anomaly A pixel value of 1 indicates: at this place there is most certainly no static anomaly OBJ_SET [N]: set of object sets. For each image an object set will be created. Each object in the set (static anomalies are not included) will be classified, whether it is considered as a particle or not.

INSPECTION_RESULT: the final inspection result will be calculated upon the information in the object sets OBJ_SET [N].

Parameters:

| Parameter name | Value for solution | Value for suspension |
|---|---|---|
| mean_mx_win | 15 | 15 |
| mean_my_win | 3 | 3 |
| bin_thresh_interval_start | 100 | 100 |
| bin_thresh_interval_end | 160 | 160 |
| area_thresh | 6 | 16 |
| kernel_mx | 2 | 2 |
| kernel_my | 11 | 11 |
| statics_thresh | 1 | 1 |
| max_no_of_particles_per_image | 0 | 0 |

General Classification Strategy:

By default the system assumes, that the container is NOGO. If it is possible to perform all inspection steps the following rules will be applied to figure out, whether the container fulfils all requirements to be classified as GO:

One particular object will be classified as particle, if its area is larger than a certain threshold area_thresh.

One particular image in the image sequence is classified as GO, if the number of detected particles in the affected object set is less or equal a certain threshold max_no_of_particles_per_image.

The inspected container is classified as GO if all images in the image sequence are classified as GO.

Basic Flow of Processing:

1) Processing Step #1

```
IM_ACCU         := all pixels set to 0
IM_MASK_STATICS := all set to 0xff
``` for each image in the image sequence do

```
IM_SRC_FIL [i] := transform (IM_SRC [i]);
   // for reducing the influence of the quantization
   // errors caused by the CMOS chip
IM_SRC_MEAN [i] := calculate_mean_value_image (IM_SRC_FIL [i]);
   // rectangular filter size of mean filter:
   // nx_win = (2 * mean_mx_win) + 1;
   // ny_win = (2 * mean_my_win) + 1;
IM_DIFF [i] := calculate_difference_image (IM_SRC_MEAN [i],
                   IM_SRC_FIL [i]);
```

-continued

```
// difference (or "local contrast") image resulting
// from subtraction of IM_SRC_MEAN [i] and
// IM_SRC_FIL [i]. In this difference image it is
// possible to define different thresholds for "dark"
// anomalies and "bright" anomalies pixels. Pixels
// having a value (difference) within the interval
// [bin_thresh_interval_start..bin_thresh_interval_end]
// are supposed to be no anomaly; pixels having values
// outside the interval are supposed to be an anomaly
IM_BIN_RAW [i] := calculate_binary_image(IM_DIFF [i],
                        bin_thresh_interval_start,
                        bin_thresh_interval_end);
    // binary image showing possible anomalies:
    // pixel value == 0: no anomaly
    // pixel value != 0: anomaly
(dx,dy) := EVAL_DISLOCATION (IM_PROTO, IM_BIN_RAW [i]);
    // calculates a dx/dy for alignment
IM_BIN [i] := aligned_copy_of (IM_BIN_RAW [i], dx, dy);
IM_MASK [i] := expand_image (IM_BIN [i], kernel_mx,
kernel_my);
    // IM_MASK [i] := all set to 0
    // for each pixel at (y,x) in IM_BIN [i] do
    //      if value != 0 then
    //          draw rectangle to IM_MASK [i], with y,x as
                center
    //          and horizontal extents kernel_mx*2 + 1
    //          and vertical extents kernel_my*2 + 1
    //      endif
    // endfor
IM_ACCU := increment_accumulator (IM_MASK [i]);
    // for each pixel at (y,x) do
    //      if IM_MASK [i][y][x] != 0 then
    //          IM_ACCU [y][x] ++;
    //      endif
    // endfor
endfor;
IM_MASK_STATICS := set_level (IM_ACCU, statics_thresh);
    // for each pixel at (y,x) in IM_ACCU do
    //      if (IM_ACCU [y][x] <= statics_thresh) then
    //          At this place no statics
    //          IM_MASK_STATICS [y][x] := 0xff // no statics
    //      else
    //          At this place statics
    //          IM_MASK_STATICS [y][x] := 0x00 // statics
    //      endif
    // endfor
```

2) Processing Step #2 for each image in the image sequence do

```
IM_BIN_EXT [i] := IM_BIN [i] BITAND IM_MASK_STATICS;
    // only anomalies at places without statics will survive
    // the BITAND function
OBJ_SET[i] := extract object set (IM_BIN_EXT);
    // create recursive object structure of objects
classify_object_set (OBJ_SET[i])
    // evaluate recursive object structure and classify
    // object whether they are to be considered as particle
    // or noise
endfor;
perform_final_classification (OBJ_SET [all],
            max_no_of_particles_per_image);
    // all object sets must have an amount of particles
    // which is less or equal to the threshold
    // max_no_of_particles_per_image
```

Presently, the cameras 36 and 38 are orientated towards a respective light source, viz. the light sources designated the reference numerals 40 and 42, respectively. The light sources 40 and 42 emit electromagnetic radiation substantially within a frequency range that the cameras 36 and 38 are sensitive to. The light sources 40 and 42 preferably cover the part of the field of view of the camera wherein the container 16 is visible to the camera. The light sources 40 and 42 are preferably generally uniform, meaning that the light is distributed substantially uniformly in the field of view of a respective camera and may provide continuous or strobe light.

In the presently preferred embodiment of the present invention, the light is strobed or flashed at a frequency of 100 Hz and the flash or strobe light is synchronised with the camera so that the camera records images at a frequency of 100 Hz, i.e. corresponding to the frequency of the strobe light. In other embodiments, other frequencies than 100 Hz may be used.

The electromagnetic radiation emitted from the light sources 40 and 42 are preferably with the visible spectrum, but may also comprise radiation within the ultraviolet and infrared spectrum. The choice of wave length of the light emitted from the light sources 40 and 42 depends on the nature of the material used to form the containers 16 since some materials are not transparent or translucent to light emitted in the ultraviolet spectrum, infrared spectrum or near-infrared spectrum.

The holders 14 will be described in greater detail with reference to FIG. 5 below.

After the container 16 has been inspected and the container 16 has been verified as being either good or bad, the container is received on a third wheel 46 similar to the wheels 24 and 26. The container is hereafter received in a conveyor 48 bringing the container to a receiving section beginning with the wheel 50. Alternatively, the conveyor 48 may be used to return a specific container 16 deemed to be re-examined, i.e. a container 16 where at least two of the image analysis processes have resulted in different outcomes. More cameras may be used if a higher degree of certainty of correct detection is required or if different area are to be inspected or detected separately.

In the presently preferred embodiment of the present invention, a specific device is used to return the containers to the inspection machine, e.g. a mechanical switch or ejector, preferably a wheel or clips-belt is used.

A limit to the number of times a specific container may be returned to the inspection machine may be defined. This will prevent the machine to fill up with containers where the inspection machine is not able to obtain two or more establishments of presence or non-presence of objects or faults in a specific container.

When a specific container is to be returned to the inspection machine, the feeding system must be instructed to stop feeding new containers to the inspection machine, so as to allow the insertion of the container to be re-inspected.

The container 16 is conveyed by the conveyor 52 past a number of drop stations, all of which are designated the reference numeral 54. In FIG. 1, three drop stations have been illustrated where one may receive containers that have been identified as comprising unwanted objects or material, alternatively having faults in the material used to form the containers, and the others for different purposes, such as storing prior to packaging, alternatively directly into packages.

The operation of the inspection machine may be controlled by an external computer device 56. The computer 56 may include input capabilities, such as keyboards, pointing devices, one or more touch-screens, buttons or the like or any combinations thereof. The computer 56 may include information regarding the product to be inspected, and collect information regarding the operation of the inspection machine, such as statistics of the inspection including the number of containers inspected, number of rejects and the like. Also, the computer device 56 may display the view of the cameras 36 and/or 38.

Figure 1A:
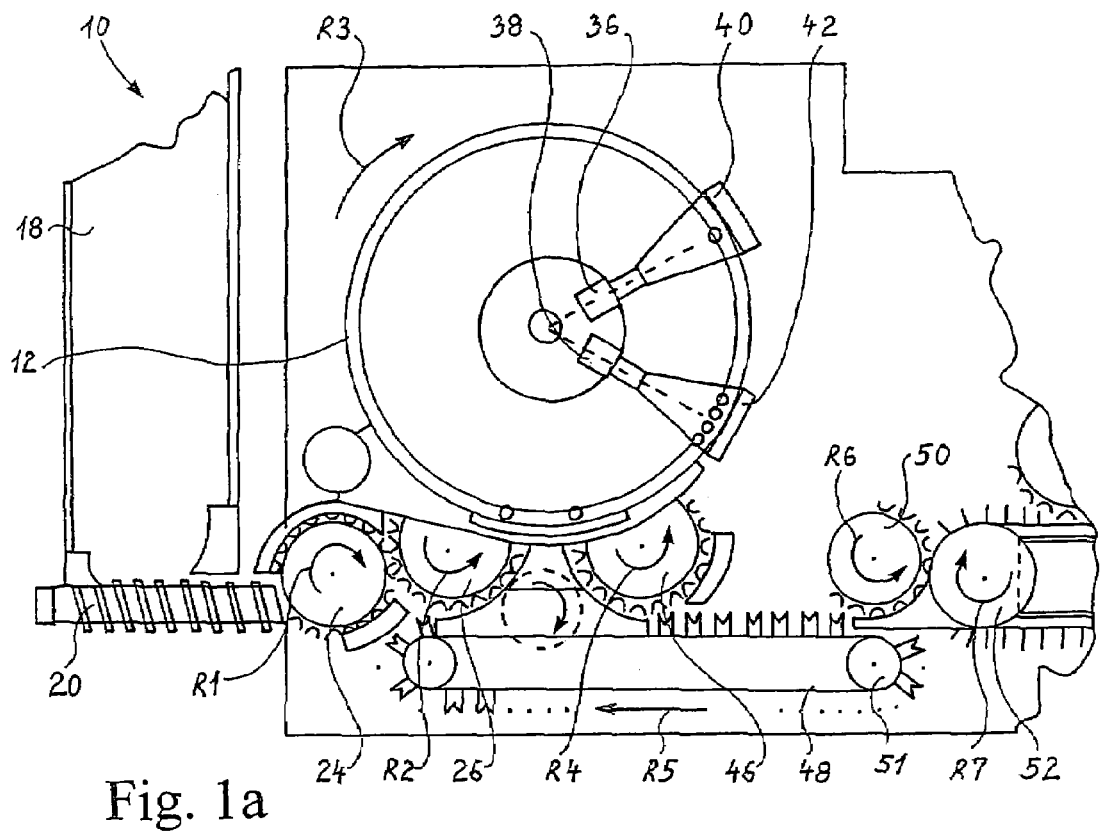
FIG. 1a is a schematic top view of a part of the machine of FIG. 1.

FIG. 1a is a schematic top view of a part of the inspection machine 10 shown in FIG. 1. The containers are brought from the container storage or feeding system 18 via the worm or screw 20 on to the first wheel 24 rotating in the direction of the arrow R1. When the container 16 is brought into the point where the wheel 24 is in contact with the wheel 26, rotating in the direction of the arrow R2, the container 16 is received on to the wheel 26. The wheel 26 rotates and delivers the container 16 to the carrousel 12. The carrousel 12 rotates in the direction of the arrow R3 bringing the container 16 into the field of view of the first camera 36 and afterwards into the field of view of the second camera 38.

Along the path of travel of the carrousel 12, the container 16 may be rotated or spun in one or both directions, i.e. clockwise or counter-clockwise, at varying or constant speeds, alternatively alternating directions.

In the presently preferred embodiment of the present invention, the containers are rotated at a speed of maximum 10,000 rpm depending on the contents of the container. Provided a container is filled with a suspension fluid, the container is rotated at a speed of 5-7,000 rpm while a partly filled container is rotated at a speed of around 1,000 rpm in order not to create air bubbles in the fluid or liquid in the container while ensuring that the fluid or liquid in the container does not form a complete vortex and no fluid is found on the bottom of the container while the container is being rotated. The speed at which the container is rotated also depends on the viscosity of the fluid or liquid in the container.

The carrousel is rotated at a speed so that a specific number of containers is inspected within a given period of time, such as 200 items per minute or 400 items per minute or 600 items per minute or 800 items per minute or 1200 items per minute, or even higher. The number of items per minute inspected may depend on the time used for rotating each of the containers as fluids having a high viscosity may require longer period of rotation compared to fluids or liquids having a low viscosity.

Figure 2:
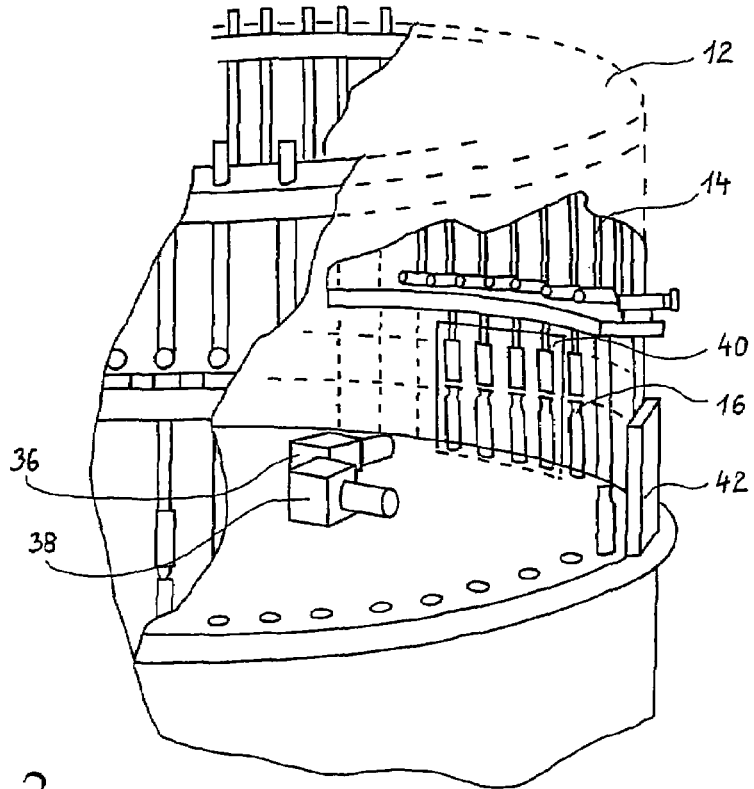
FIG. 2 is a schematic partial view of the carrousel of the machine of FIG. 1.

FIG. 2 is a partly cut-through view of the carrousel 12 of the inspection machine 10 of FIG. 1. The figure illustrates the placement of the cameras 36 and 38 relative to the light sources 40 and 42. The field of view of the cameras 36 and 38 may include more than one holder 14 with a corresponding container 16. As previously mentioned, the light sources 40 and 42 substantially cover the field of view of the cameras 36 and 38, respectively.

Figure 3:
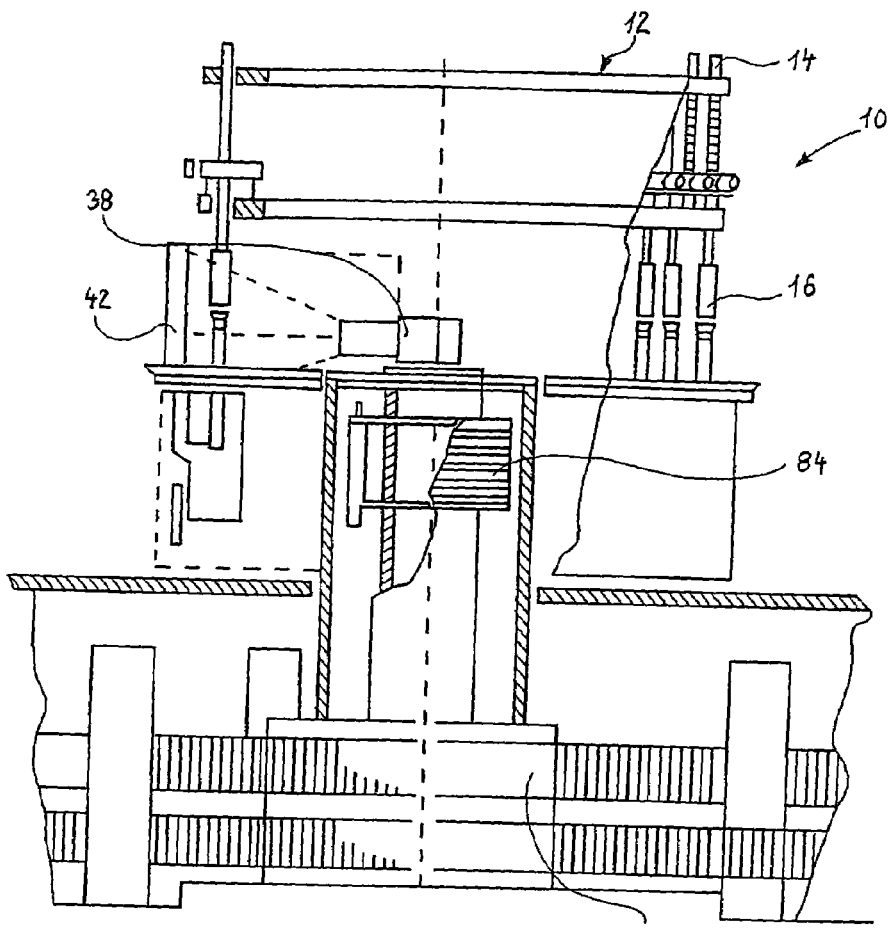
FIG. 3 is a schematic partial view of the machine of FIG. 1.

FIG. 3 is a schematic cut-through view of the carrousel 12 of FIG. 1 and also of a motor for driving the carrousel 12. In a presently preferred embodiment of the present invention, the motor 58 is from the company NSK and is of a type no. M-YS5120GN011, with an ESA25 driver unit. However, other motors or driver units may be utilised in other embodiments of the present invention.

Figure 5:
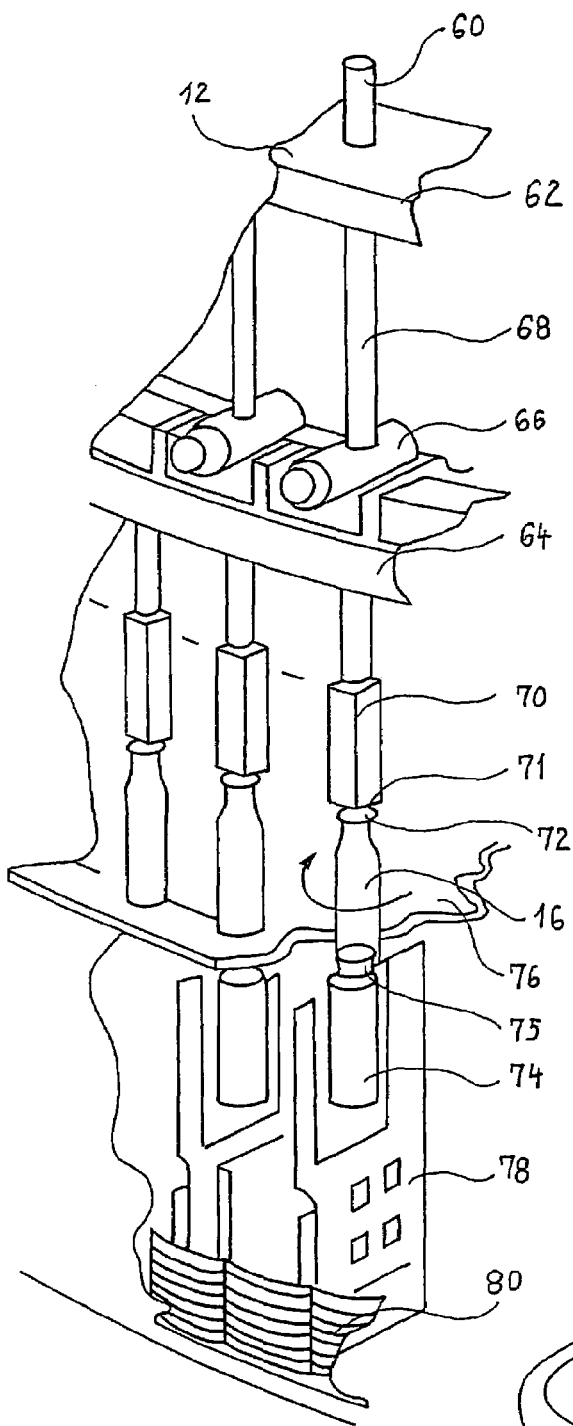
FIG. 5 is schematic detailed view of a holder of the carrousel in the inspection machine.

FIG. 5 is a schematic view of the carrousel 12 where a rod 60 extends from a top ring 62 through a bottom ring 64. The rod 60 is fitted with a blocking device 66 limiting the downward motion of the rod 60. A spring 68 pushes the rod 60 downwards. At the distal end of the rod 60, an interface part 70 is mounted. The interface part 70 comprises a rotational part 72 for receiving a top part of the container 16.

The container 16 is held between the rotational part 72 and a receiving part 75 of a rotating motor 74 mounted below a surface 76 of the carrousel 12. The rotational part 72 includes a spring to hold the container in place.

The rotation motor 74 rotates the container 16 in either clockwise or counter-clockwise direction relative to the longitudinal axis of the container and/or the rod 60. Each of the motors 74 are controlled by an individual control unit that may be constituted by a microprocessor or microcontroller including software for controlling the operation of the motor 74. All of the controller units 74 are interconnected in a network such as a CAN-bus network where the electrical connections between the controller units 78 are constituted by a band 80, also connecting each of the controller units 78 to the root controller 88.

When a container 16 is to be loaded in-between the motor 74 and the rotating part 72 of the interface part 70, the rod 60 must be lifted so that the container 16 may be inserted in-between these parts.

As the carrousel 12 rotates, the distal end of the blocking device 66 engages the rising part 32 of the protruding part 30, and the rod 60 is displaced upwardly. When the holder 14 is near the end of the rising part 32, the container 16 will be near the carrousel exit point 44, and the third wheel 46 removes the container 16 from the carrousel 12. When the holder 14 approaches the drop point 28, the rotational part 72 and the rotation motor 74 are still separated sufficiently to receive a container 16 from the second wheel 26. When the container 16 has been received between the rotational part 72 and the rotation motor 74, the spring 68 will press down the rod 60 while the blocking device 66 slides down the descending part 34 of the protecting part 30.

Figure 4:
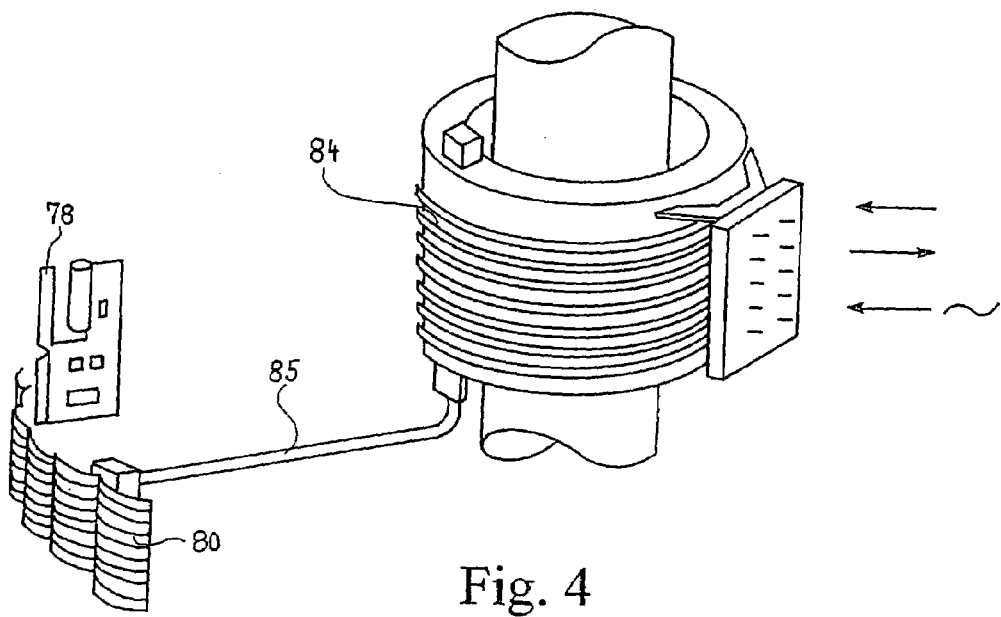
FIG. 4 is a schematic view of a slip ring and a controller.

FIG. 4 is a schematic view of the slip ring 84 of the inspection machine 10. The slip ring 84 is connected to the band 80 via an electrical connection 85. In the presently preferred embodiment of the present invention a slip ring from the AC6098 series from Northrop Grumman is used.

Figure 6:
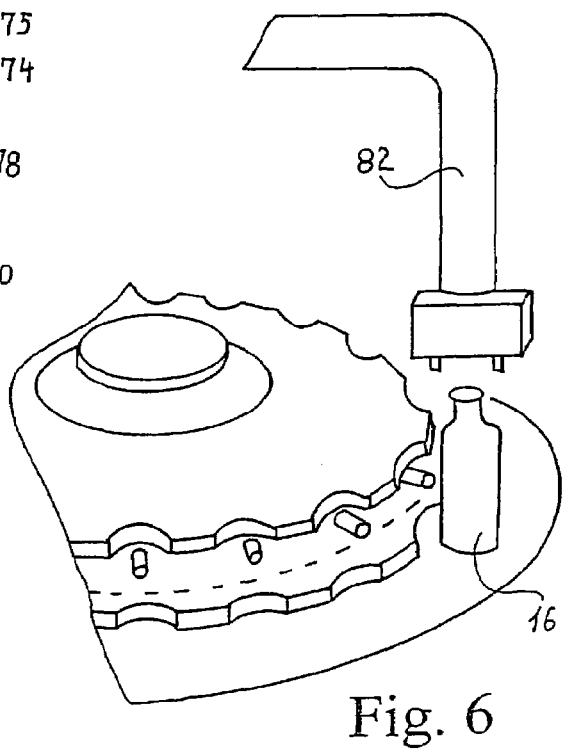
FIG. 6 is a schematic view of a return system.

FIG. 6 is a schematic representation of an embodiment of a return system for returning containers 16 where the images process from the two cameras 36 and 38 have resulted in two different outcomes. A detector mounted on an arm 82 detects the presence of a container 16 so that the container may be conveyed from the wheel 46 either back to one of the wheels 24 or 26 or back into the container storage of the feeding system 18.

Figure 7:
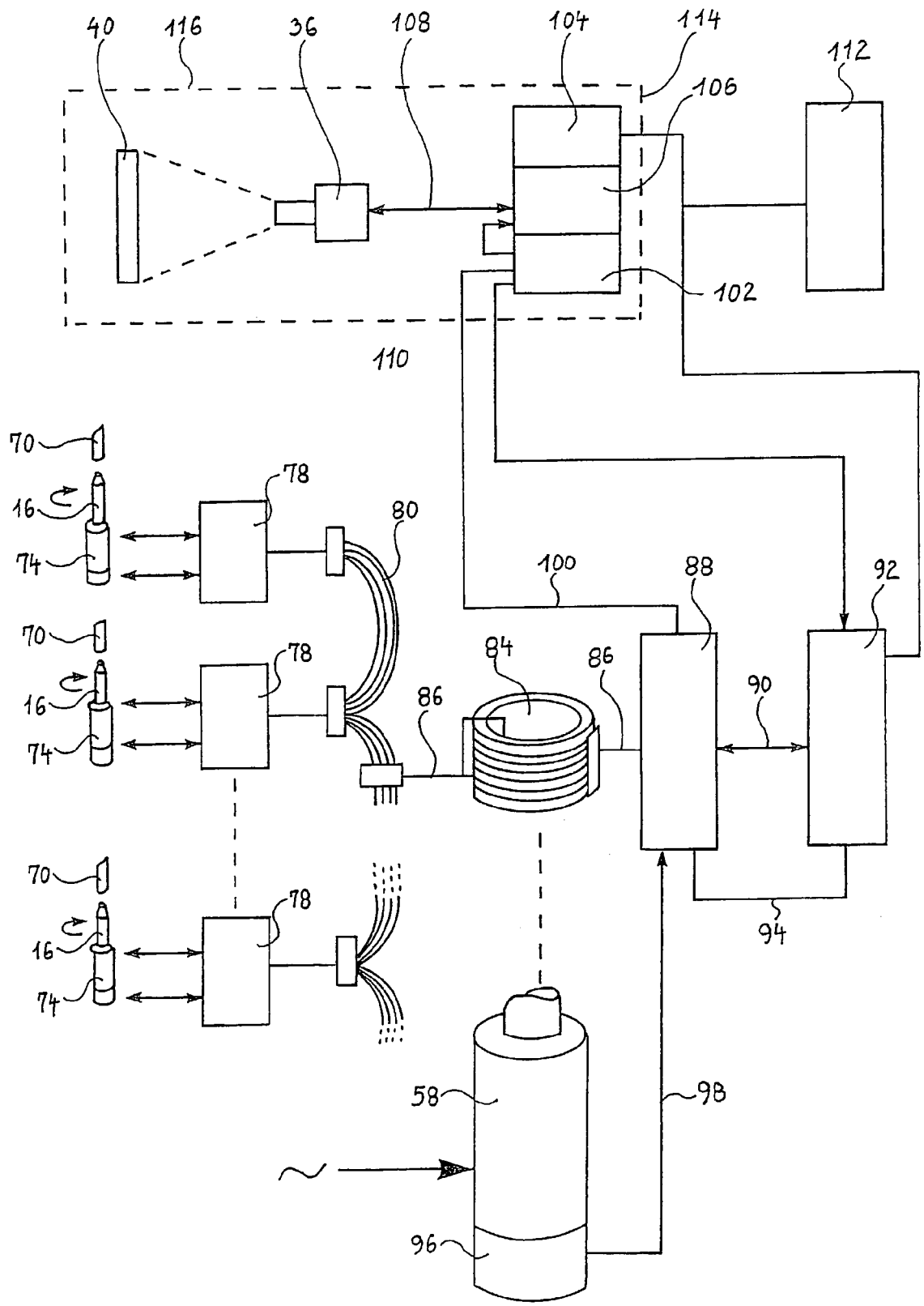
FIG. 7 is a schematic block diagram of the inspection machine.

FIG. 7 is a diagram illustrating the components used for the inspection machine 10 according to the present invention.

The rotating motors 74 are individually controlled by a controller unit 78. The controller unit 78 controls the direction and the speed in which the rotation motor 74 rotates. Each of the controller units 78 are connected to two neighbouring controller units via the band 80 in a CAN-bus network. The band 80 has an external connection via a CAN-bus 86 connection to a slip ring 84. The root controller 88 communicates to the individual controller units 78. In the presently preferred embodiment of the present invention, the rotating motors are from the company Faulhaber, type: 3564 K 048 B K312. The choice of motor depends on the dimensions and/or mass of the object, i.e. the container and/or the fluid or liquid, to be rotated.

The slip ring 84 is connected both via a digital 10 and the CAN-bus 86 to a root controller 88. The root controller 88 communicates with a PLC via both a digital IO 90 and a CAN-bus connection 94. The root controller 88 is further connected to an acquisition controller 102 that controls the acquisition of the images from the cameras 36 and 38. The connection between the root controller 88 and the acquisition controller 102 is in the presently preferred embodiment of the present invention constituted by a CAN-bus network connection 100.

The vision system is generally denoted 116 and visualised by the punctuated line surrounding the elements constituting the vision part of the inspection machine 10. The acquisition controller 102 is placed in or connected to a particle inspection unit 104, constituted by a computer. The acquisition controller 102 is further connected to a frame grabber 106 registering the images from either one or more of the cameras 36 and 38 received through a camera link 108. The camera link 108 may be constituted by a wireless or wired connection. The acquisition controller 102 is connected to the framegrabber 106 via a digital IO connection 110. The root controller 88 controls the operation of the acquisition controller 102.

The elements constituting the vision systems 116 may be identical or different, meaning that e.g. different processing units may be required, or desired, for processing of images captured by different cameras.

The camera or cameras may detect objects or faults having a diameter or size larger than 10 micrometer, in the presently preferred embodiment of the present invention, objects or faults having a size down to 50 micrometer may be detected.

The slip ring 84 is connected to the motor for the carrousel 58. The motor 58 comprises an encoder 96.

The root controller 88 performs synchronisation of hardware timers in both the individual controller units 78 and the acquisition controller 102. The root controller 88 broadcasts a data package comprising the position of the carrousel 12 read from the encoder 96 along with the time at which the position was recorded. This information or data package is preferably broadcast periodically, such as every 5 ms.

The root controller 88 is connected to a PLC 92 via a digital I/O 90 and via a CAN-bus connection 94. The PLC 92 controls the entire inspection machine 10, while the acquisition controller 102 in the particle inspection PC 104 and the spin or rotation motors 74 are controlled by the root controller 88.

A SCADA system 112 is connected to the inspection PC 104 and to the PLC 92 via a local area network 114, currently preferably constituted by an Ethernet network and/or implemented as a Profibus solution. The network connection may be constituted by wireless or wired network connection. The SCADA 112 controls the operation of the PLC 92 and may comprise a database including product information and process logging information.

The cameras 36 and 38 operate in free run mode, meaning that the cameras do not need to receive a trigger signal in order to record an image. In the presently preferred embodiment of the present invention, the images are recorded at 128 Hz, giving 7.8 ms between each frame or image. Different recording rates are of course possible. When the camera initiates a recording of an image or frame, a sync-signal is sent to the acquisition controller 102 via the frame grabber 106, so that the acquisition controller 102 may establish when a new image recording has been initiated.

As the transmission of an entire image recorded by a camera is contemplated to require a large bandwidth on the transmission line, e.g. a cable or wire, it may be desirable to limit the amount of data transmitted. One limitation may be found by choosing to record grey-scale or b/w images. Another may be to transmit only a part of an image, i.e. a sub-image. The sub-image may then comprise the part of the entire image recorded by the camera where the object to be inspected, i.e. the container, is to be found.

The acquisition controller 102 is able to predict or calculate the position of the carrousel 12 prior to recording an image from either of the cameras 36 or 38 and thereby determining where a sub-image of the image recorded by the cameras 36 and 38 are to be located in order for the sub-image to comprise the container 16.

The size of the sub-image is determined individually for each product to be inspected, as two specific products not necessarily having the same overall geometrical configuration.

In the presently preferred embodiment of the present invention a camera from the company Mikrotron, type: MC1310, is used. The camera produces images having a resolution of 1280×1024 pixels, with a quantification of 8 bit/pixel. The dimensions of the sub-image are preferably supplied to the camera prior to initiating the inspection. It is not required to supply the dimensions after each power-down of the machine as the values may be stored in non-volatile memory.

In the presently preferred embodiment of the present invention, the sub-image is defined as a rectangular image. Also, only one sub-image is acquired at one time. However, embodiments where a number of sub-images are selected may be envisioned. A number of sub-images may enable a system to inspect several containers simultaneously.

The sub-image is selected and controlled via firmware loaded into an EEPROM in the camera, that is loaded into a FPGA in the camera when the camera boots. Also, the values concerning the sub-image may be transferred from the SCADA PC 112 or from the inspection PC 104 to the camera during boot.

The sub-image may be moved along the y-axis of the image in the camera. The starting and finishing coordinates of the sub-image is determined individually for each product type to be inspected. The dimensions and the coordinates are part of an acquisition profile for a specific product that the acquisition controller 102 may use to control the image capture or recording. The acquisition profile may be loaded into the acquisition controller 102 during system start up or boot from either the inspection PC 104 or the SCADA PC 112.

The acquisition controller 102 controls the acquisition or recording of the images from the camera. The sub-image is controlled based on the information in the acquisition profile and time-stamp information regarding the position of the carousel 12 received from the root controller 88. Sub-image control based on image analysis may be envisioned and is considered part of the present invention.

Other sub-images than rectangular or square may be envisioned, such as sub-images precisely corresponding to the outline of a container.

Generally, there may be N rotation or spin motors 74 and corresponding controller units 78. In the presently preferred embodiment of the present invention, all of the N rotation or spin motors 74 and the corresponding controller unit 78 are identical. N may be any natural number, but a number between 20 and 150 are preferred, such as 40, 50 or 100. Carrousels 12 adapted for inspecting large containers or bottles may comprise a lower number of stations than a carrousel adapted for inspecting smaller containers or bottles.

The criteria for moving the sub-image, is that the sub-image must follow the container to be inspected from the moment the container enters the field of view of the camera until it leaves the cameras field of view.

In the following, the Root Controller will be mentioned as Master, while the Motor Controller and the Acquisition Controller is mentioned as Slave.

The master performs synchronisation of the hardware timer on each Slave via the CAN bus, so that the Master and the Slaves have the same time setting.

The Master cyclically broadcasts, presently every 5 ms, the following information: (v_pos, t_pos), where v_pos is the position of the inspection carrousel read from the encoder of the carrousel motor, and t_pos is the time at which the position is read.

The information broadcast from the Master is stored in each of the Slaves in a data structure pt_fifo, a position-time FIFO with a depth of 2 tuples (v_pos/t_pos). Using the pt_fifo a Slave may calculate v_pos(t_pos), i.e. the position of the inspection carrousel as a function of time, which generally is an extrapolation of the available information.

The camera operates in a free-run mode, meaning that the camera does not need a trigger signal for recording an image. Presently, the camera records images at a frequency of 128 Hz giving 7.8 ms between each image. Each image recording is initiated with the generation of a vertical sync-signal, which is sent to the Acquisition Controller via the Framegrabber, so that the Acquisition Controller knows when the digitisation of a new image is commenced by the camera.

The Acquisition Controller is able to predict the position of the inspection carrousel when the next image is being recorded and thereby also when and how much the sub-image is to be moved before the subsequent image will be recorded in order for the sub-image to substantially follow the container.

The control of the sub-image is handled by the Acquisition Controller based on the time-stamped information received from the Root Controller, as described earlier, and from data in an Acquisition Profile, data structure acq_prof. An Acquisition Profile is a table of sectors ordered by the position of the inspection carrousel. One sector is defined as 360/N part of the inspection carrousel. The inspection carrousel comprises N stations, as seen in FIG. 8, N being the number of stations, typically 40, 50 or 100. For each sector the following data is stored in the Acquisition Profile acq_prof:

v_pos_1 start position of sector relative to carrousel motor encoder.

v_pos_2 stop position of sector relative to carrousel motor encoder.

obj_id object ID, corresponding to station ID.

v_acq_1 start position of subimage in camera image at v_pos_1.

v_acq_2 stop position of subimage in camera image at v_pos_2.

Basic calculations in connection with the recording of images:

t_per_image: the time between two normal sync pulses (images are acquired at the sync signal)

pt_fifo: position time fifo driven by communication acq_prof: acquisition profile v_acq_eff: actual number of pulses been generated by the module (initial value=0)

The following calculations are carried out on the Acquisition Controller at each vertical sync generated by the camera:

```
/*
* calculate the position of the carousel
* at the time where the next image gets acquired
*/
v_pos_next = calculate_position_of_carousell (pt_fifo,
        t_now + t_per_image);
if (v_pos_next >= 0) {
    /*
    * position forcasting delivered valid result
    */
int obj_id_next = -1;
int v_acq_next = -1;
/*
* this function will find the sector with v_pos_next lying
* inside.
* the function calculates the shift value v_acq_next
* the function returns obj_id_next
*/
int i_tab_sector = AcqProf_get_info_from_v_pos (acq_prof,
        v_pos_next,
        &obj_id_next,
```

-continued

```
        &v_acq_next);
    if (obj_id_next >= 0) {
        /*
        * there is an object to be acquired
        */
DO_ACQ_SEQ (1); // acquisition signal for PC
/*
* calculate number of increment pulses to be generated for
* next image
*/
d_acq = (v_acq_next >= 0) ? (v_acq_next - p->v_acq_eff) : 0;
if (d_acq > 0) {
    /*
    * generate required number of pulses to shift subimage
    */
    generate_n_pulses (d_acq);
    p->v_acq_eff = v_acq_next; // update internal
        };
    } else {
        /*
        * there is no object to be acquired
        */
        DO_ACQ_SEQ (0); // acquisition signal for PC
        p->v_acq_eff = 0;
    };
} else {
    /*
    * position forcasting delivered invalid result
    */
    DO_ACQ_SEQ (0); // acquisition signal for PC
    p->v_acq_eff = 0;
};
```

The function DO_ACQ_SEQ( ) controls the digital signal DO_ACQ_SEQ from the Acquisition Controller to the Frame-grabber; the arguments of the function gives the state of the corresponding digital signal.

When the signal is high (1), the framegrabber records images from the camera, when the signal is low (0), the Framegrabber ignores images from the camera-meaning that the signal acts as a gate for the images.

A specific carrousel may be adapted for receiving a bottle or container size within an interval, thereby not limiting the capability of the carrousel to receive only one specific size of containers, e.g. by providing a plurality of adaptors or receivers for the rotational part 72 of the motor unit and/or the receiving part 75.

The inspection system or machine may be placed inline with other processing systems or machines, such as package or filling machines.

FIGS. 9*a* to 9*c* is a schematic illustration of a sequence of images recorded by a camera. The container is moved along the y-axis of the camera image frame and a sequence of images and sub-images are recorded. The sub-images are transmitted to an image processing unit, as described earlier.

Figure 10:
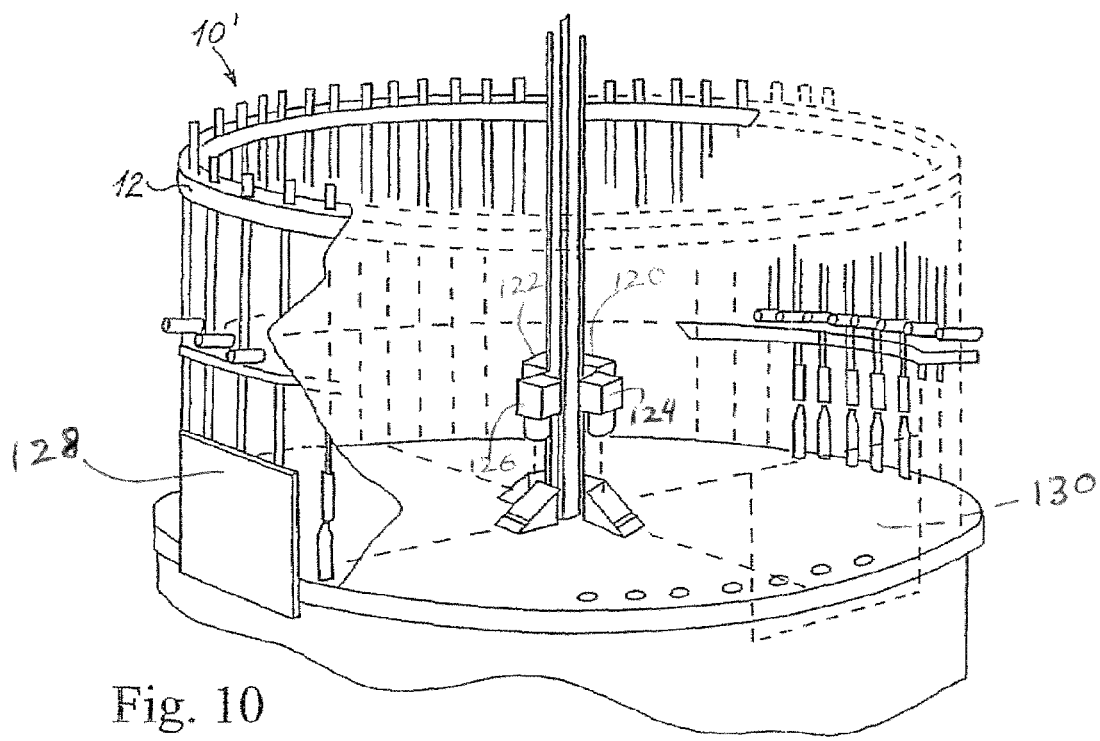
FIG. 10 is a schematic cut-through view of a carrousel of an inspection machine having an alternative camera configuration.

FIG. 10 schematically illustrates a carrousel 12 of an inspection machine 10' where an alternative camera configuration is used. Inside the carrousel 12 four cameras 120,122, 124,126 are positioned. In the embodiment illustrated in FIG. 10, the cameras 120,122,124,126 are placed so that the fields of view defined by the cameras 120,122,124,126 are directed towards the bottom of the carrousel 12. In order for the cameras 120,122,124,126 to inspect the containers, four mirrors, of which only two are visible in the figure, namely 128 and 130, are positioned so that the cameras may inspect the containers. In an alternative embodiment, all or some of the cameras are positioned so that the fields of view are directed directly towards the containers, e.g. such as the cameras illustrated in FIG. 1. In other embodiments, filters, prisms or other optical components may be placed in the field of view of the cameras, i.e. between the camera and the container so as to alter or modify the light transmitted from a light source to the camera or cameras.

Figure 11:
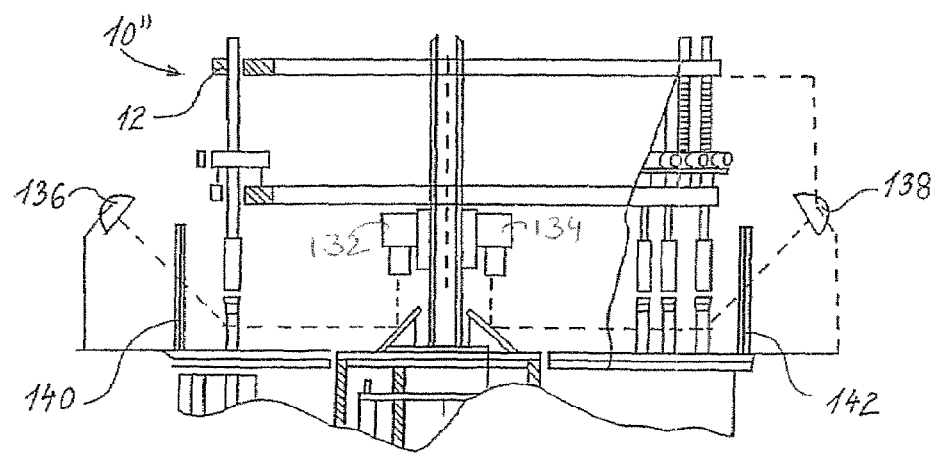
FIG. 11 is a schematic cut-through view of an inspection machine having an alternative configuration of cameras and light sources.

In FIG. 11 illustrates an inspection machine 10″ having a carrousel 12. Cameras 132 and 134 are positioned similarly to those illustrated in FIG. 10, although in alternative embodiments the cameras 132 and 134 may be positioned as those illustrated e.g. in FIG. 1. Two light sources 136 and 138 are positioned so that the light emitted by the light sources 136 and 138 is not directed directly towards the field of view defined by the corresponding camera. This configuration is contemplated to enable inspections for objects such as fibres which inspections may not be possible with the configuration illustrated in e.g. FIG. 1a.

Figure 12:
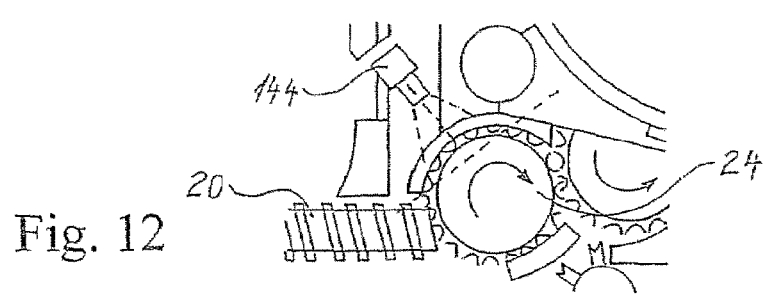
FIG. 12 is a schematic top-view of an inspection machine having a camera for cosmetic inspections.

FIG. 12 schematically illustrated an embodiment of an inspection machine including a camera 144 for performing inspections of the containers before the containers enter the carousel. Reasons for performing an initial inspection may be to detect broken or damaged containers that may be destroyed or more broken when being held by the holders in the carousel. The camera is preferably placed near the end of the screw 20 so that the containers may be ejected or rejected before they enter the carousel. In the embodiment illustrated in FIG. 12, the camera inspects the containers while they are held in the wheel 24. The inspection performed by the camera 144 may be controlled by the same computer or device that performs the inspection by the cameras positioned within the carousel, preferably, the inspection performed by the camera 144 is controlled by a separate device or computer.

The invention claimed is:

1. A method of detecting unwanted objects or faults in a plurality of containers including a fluid or liquid, said method comprising the steps of:
   providing a path of travel along which said plurality of containers are conveyed;
   moving said plurality of containers along said path of travel;
   providing a light source emitting light of a specific spectral distribution, said light source being positioned at one side of said path of travel, wherein said containers are at least partly transparent or translucent to the light at said specific spectral distribution, said fluid or liquid being at least partly transparent or translucent to light at said specific spectral distribution;
   providing a first camera including a CMOS chip for detecting light at said specific spectral distribution emitted from said light source, wherein said first camera defines a field of view, said path of travel intersects said field of view, and said CMOS chip produces a digital image comprising a specific number of pixels;
      rotating each of said containers so as to bring said fluid contained in each of said containers in motion;
      stopping said rotation of each of said containers said fluid still rotating therein;
   said first camera registering a sequence of digital images as said container passes between said light source and said camera;
   selecting a part of each of said digital images, said part substantially corresponding to the outline of a specific container;
   transmitting each of said parts to a digital image processing unit; and
   processing a sequence of said parts of digital images so as to detect either the presence or absence of said unwanted objects or faults in said specific container.

2. The method according to claim 1, wherein said processing is constituted by said digital image processing unit comparing at least two of said parts of two specific digital images to detect unwanted objects or faults in said specific container.

3. The method according to claim 1, wherein said processing is constituted by said digital image processing unit analyzing at least one digital image to detect unwanted objects or faults in said specific container.

4. The method according to claim 1, wherein said processing is constituted by a subtraction of two images in sequence or out of sequence.

5. The method according to claim 1, wherein said processing is constituted by a comparison of said part of a specific digital image to a reference image for detecting unwanted objects or faults in said specific container.

6. The method according to claim 1, wherein said containers are conveyed at a substantially constant speed along said path of travel.

7. The method according to claim 1, further comprising:
   providing a second camera including a second CMOS chip for detecting light at said specific spectral distribution emitted from a second light source, a second line of sight being defined between said second light source and said second camera, wherein said path of travel intersects with said second line of sight; and said second CMOS chip produces a digital image comprising a second specific number of pixels;
   wherein said second camera registers a second sequence of frames constituting a second multitude of digital images as said container passes between said second light source and said second camera;
      selecting a second part of each of said digital images of said second sequence, said second part substantially corresponding to the outline of said specific container;
      transmitting each of said second parts to said digital image processing unit;
      said digital image processing unit processing said second multitude of said parts of digital images so as to detect said unwanted objects or faults in said specific container; and
      comparing the result of said second processing to said first processing in order to confirm the result of said first processing.

8. A method of detecting unwanted objects or faults in a plurality of containers including a fluid or liquid, said method comprising the steps of:
   providing a path of travel along which said plurality of containers are conveyed;
   moving said plurality of containers along said path of travel;
   providing a first light source emitting light of a specific spectral distribution, said light source being positioned at one side of said path of travel, wherein said containers are at least partly transparent or translucent to light at said specific spectral distribution, and said fluid or liquid is at least partly transparent or translucent to light at said specific spectral distribution;
   providing a second light source emitting light of said specific spectral distribution, said second light source being positioned at one side of said path of travel;
   providing a first light detection device for detecting light at said specific spectral distribution emitted from said first light source, wherein said first light detection device defines a first field of view, said path of travel intersects said first field of view and said first light detection device produces a first digital image comprising a specific number of pixels;
   providing a second light detection device for detecting light at said specific spectral distribution emitted from said second light source, wherein said second light detection device defines a second field of view, said path of travel intersects said second field of view, and said second light detection device produces a second digital image comprising a second specific number of pixels;

said first and said second light detection device registering a first and second sequence of digital images as said container passes said first and said second field of view respectively;

selecting a part of each of said digital images of said first and said second sequence, said part substantially corresponding to the outline of a specific container;

transmitting each of said parts to a digital image processing unit;

said digital image processing unit processing each of said parts of said digital images so as to detect said unwanted objects or faults in said specific container; and said processing resulting in either an establishment of an object or fault present or not present in said specific container.

9. The method according to claim 8, wherein said first and said second light detection units are constituted by cameras each including at least one CMOS chip for producing said first and said second digital images.

10. An apparatus for detecting unwanted objects or faults in a plurality of containers including a fluid or liquid, said apparatus comprising:

a frame;

a conveyor mounted in said frame constituting a path of travel for said plurality of containers, said conveyor defining an input and a corresponding output, said input receiving said plurality of containers, said output outputting said plurality of containers;

a first light source emitting light of a specific spectral distribution mounted in said frame, wherein said first light source is positioned at one side of said path of travel, said containers are at least partly transparent or translucent to light at said specific spectral distribution, and said fluid or liquid is at least partly transparent or translucent to light at said specific spectral distribution;

a first camera including a first CMOS chip for detecting light at said specific spectral distribution emitted from said first light source, said first camera defining a first field of view, wherein said first camera is mounted to said frame, and said path of travel intersects said first field of view, said first CMOS chip produces a first digital image comprising a first specific number of pixels, said first camera registers first sequence of digital images as a specific container passes said first field of view; and a first digital image processing unit electrically connected to said first camera;

wherein said first camera selects a part of each of said digital images substantially corresponding to the outline of a specific container and transmits said part to said digital image processing unit;

wherein said first digital image processing unit processes a sequence of said parts of said digital images so as to detect the presence or absence of said unwanted objects or faults in said specific container.

11. The apparatus according to claim 10 wherein said conveyor is selected from the group consisting of at least one of a rotating carrousel, a belt conveyor, and a chain conveyor.

12. The apparatus according to claim 11 wherein said conveyor is directly driven by a drive mechanism selected from the group consisting of a servo motor, a step motor, a linear motor, and a gear means.

13. The apparatus according to claim 10, wherein each of said containers is rotated in either clock-wise or counter-clockwise direction by rotating means so as to bring said fluid contained in each of said containers in motion.

14. The apparatus according to claim 10, further comprising:

a second light source emitting light of said specific spectral distribution mounted in said frame, said second light source being positioned at one side of said path of travel; and a second camera including a second CMOS chip for detecting light at said specific spectral distribution emitted from said second light source, wherein said second camera defines a second field of view, said path of travel intersects said second field of view, said second CMOS chip produces a second digital image comprising a second specific number of pixels, and said second camera registers a second sequence of digital images as said specific container passes said second field of view.

15. The apparatus according to claim 10, further comprising:

a second camera including a second CMOS chip for detecting light at said specific spectral distribution emitted from said first light source, wherein said second camera defines a second field of view, said path of travel intersects said second field of view, said second CMOS chip produces a second digital image comprising a second specific number of pixels, said second camera registering a second sequence of digital images as said specific container passes said second field of view.

16. The apparatus according to claim 14, wherein:

said second camera is electrically connected to said first digital image processing unit.

17. The apparatus according to claim 14, further comprising:

a second digital image processing unit, wherein said second camera is electrically connected to said second digital image processing unit.

18. The apparatus according to claim 16, wherein:

a part of each of said second digital images substantially corresponding to the outline of a specific container is transmitted to said digital image processing unit;

one of said first and said second digital image processing units processes said second sequence of digital images so as to detect said unwanted objects or faults in said specific container;

said processing resulting in either an establishment of an object or fault present or not present in said specific container.

19. The apparatus according to claim 10, wherein:

said path of travel defines an input and a corresponding output, said input receiving said plurality of containers, said output outputting said plurality of containers;

and wherein said apparatus further comprises a return conveyor for conveying specific containers from said output to said input.

20. The apparatus according to claim 19, wherein said return conveyor is selected from the group consisting of at least one of a rotating carrousel, a belt conveyor, a chain conveyor, and a star-wheel.

21. The apparatus according to claim 11, wherein said conveyor includes a carrousel and at least one of said first camera and said second camera is positioned within said carrousel.

22. The apparatus according to claim 20, wherein said conveyor includes a carrousel, and wherein at least one of said first camera and said second camera is positioned within said carrousel.

* * * * *